United States Patent [19]
Coughlin et al.

[11] Patent Number: 6,155,485
[45] Date of Patent: Dec. 5, 2000

[54] MEDICAMENT DISPENSING STATION

[75] Inventors: Michael E. Coughlin, Overland Park, Kans.; Christopher J. Thomsen, Kansas City, Mo.; Claire P. Coughlin, Overland Park, Kans.

[73] Assignee: Scriptpro LLC, Mission, Kans.

[21] Appl. No.: 09/188,734

[22] Filed: Nov. 9, 1998

[51] Int. Cl.[7] .................................................. G06K 15/00
[52] U.S. Cl. .......................................... 235/383; 235/456
[58] Field of Search .............................. 235/375, 462.01, 235/472.01, 379, 487; 283/67, 70, 900

[56] References Cited

U.S. PATENT DOCUMENTS

| | | |
|---|---|---|
| 1,128,561 | 2/1915 | Webendorfer . |
| 2,690,856 | 10/1954 | Trondle . |
| 3,746,211 | 7/1973 | Burgess, Jr. . |
| 3,921,196 | 11/1975 | Patterson ................................. 235/375 |
| 4,284,301 | 8/1981 | Geiger et al. . |
| 4,476,381 | 10/1984 | Rubin ...................................... 235/375 |
| 4,660,824 | 4/1987 | Hermkens et al. . |
| 4,753,473 | 6/1988 | Arnett . |
| 4,810,230 | 3/1989 | Shirasawa . |
| 4,835,372 | 5/1989 | Gombrich et al. ....................... 235/375 |
| 4,857,716 | 8/1989 | Gombrich et al. ....................... 235/462 |
| 4,872,803 | 10/1989 | Asakawa . |
| 4,902,263 | 2/1990 | Ito et al. . |
| 4,918,604 | 4/1990 | Baum ................................. 364/413.01 |
| 4,958,280 | 9/1990 | Pauly et al. .............................. 364/403 |
| 5,033,785 | 7/1991 | Woolley, Jr. . |
| 5,082,268 | 1/1992 | Santoro . |
| 5,208,762 | 5/1993 | charhut et al. ........................... 364/478 |
| 5,332,275 | 7/1994 | Conway et al. . |
| 5,337,919 | 8/1994 | Spaulding et al. .......................... 221/2 |
| 5,401,059 | 3/1995 | Ferrario .................................... 283/67 |
| 5,873,488 | 2/1999 | Guerra . |
| 5,883,370 | 3/1999 | Walker et al. ........................... 235/375 |

FOREIGN PATENT DOCUMENTS

| | | |
|---|---|---|
| 53-145260 | 12/1978 | Japan . |
| 59-43743 | 10/1984 | Japan . |
| 918086 | 4/1982 | Sudan . |

*Primary Examiner*—Thien M. Le
*Attorney, Agent, or Firm*—Hovey, Williams, Timmons & Collins

[57] ABSTRACT

A preferred medicament dispensing station (10) includes a computer (16) with a bar code reader (18) and a printer (20) coupled therewith. When filling a prescription from a supply container (12) of a medicament, the bar code reader (18) scans the bar code (28) on the container (12) and a computer (16) compares the bar code data with prescription data to determine a match before activating a printer (20) to print a prescription label (30) for the prescription. The preferred station (10) also includes databases (26) including an attribute database and a language database. The computer (16) activates the printer (20) to print medicament indicia on the prescription label (30) representative of physical attributes of the medicament including a word description (32) such as the shape, color pattern, color, scoring and form and an image (34). The computer (16) is operable also to prompt the printer (20) to print prescription data on the same label or on a second label in a second language.

37 Claims, 1 Drawing Sheet

MEDICAMENT DISPENSING STATION

RELATED APPLICATIONS

Not Applicable.

FEDERALLY SPONSORED RESEARCH OR DEVELOPMENT

Not Applicable.

MICROFICHE APPENDIX

Not Applicable.

BACKGROUND OF THE INVENTION

1. Field of the Invention

The present invention relates to the field of prescription dispensing systems.

2. Description of the Prior Art

Errors in filling prescriptions are infrequent, but they do occur. Such errors can lead to serious consequences for the patient.

One source of error is that the incorrect supply container is used for filling the prescription. Another source of error is that the labels for two different prescriptions may be switched inadvertently. When this occurs, two patients receive one another's prescription.

When these errors occur, the patient may not be familiar with the medicament's appearance. Thus, even though the prescription package contains the wrong medicament, the patient is unaware of this because the patient does not know what the appearance of the proper medicament should be and, therefore, the patient takes the medicament anyway. The problem may be compounded if the prescription label is printed in a language that the patient does not understand. That is, the label may be printed in a language that the patient cannot read.

Another source of error is the failure to provide the patient with the proper auxiliary information, such as conditions, warnings, and specific instructions for use, pertinent to the medicament.

SUMMARY OF THE INVENTION

The present invention solves the prior art problems discussed above and provides a distinct advance in the state of the art. More particularly, the medicament dispensing station hereof verifies that the correct supply container has been accessed for filling the prescription, provides medicament indicia on the prescription label representative of a physical attribute of the medicament, and enables the printing of prescription data on a prescription label in a selected second language.

The preferred medicament dispensing apparatus includes a computer with a bar code reader and a printer coupled therewith. When filling a prescription from a supply container of a medicament, the bar code reader scans the bar code on the container and a computer compares the bar code data with prescription data to determine a match before activating the printer to print a prescription label for the prescription.

The preferred apparatus also includes an attribute database and a language translation database. The computer activates the printer to print medicament indicia on the prescription label representative of a physical attribute of the medicament including a word description and also an image. The computer is also operable to prompt the printer to print prescription data in a second language. On the prescription label or on a second label, the computer is also operable to print the auxiliary information pertinent to the medicament on the prescription label. Other preferred aspects of the present invention are disclosed herein.

DETAILED DESCRIPTION OF THE PREFERRED EMBODIMENT

Figure 1:
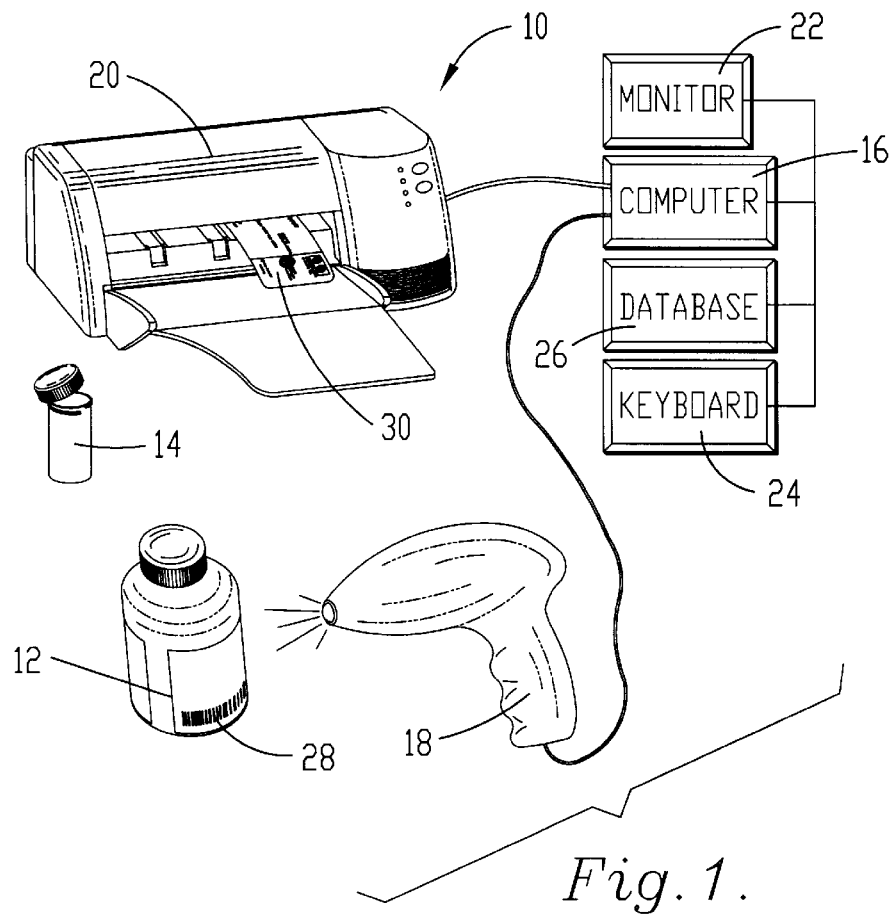
FIG. 1 is a schematic representation of the preferred medicament dispensing apparatus in accordance with the present invention, shown in use with a medicine vial and a supply container.

FIG. 1 illustrates preferred medicament dispensing apparatus 10 in accordance with the present invention. Apparatus 10 is shown in use with supply container 12 and a prescription package to be dispensed to the patient such as a medicine vial, box, jar, bottle or other package as represented by medicine vial 14.

Apparatus 10 includes computer 16 coupled with an indicia-reading device such as bar code reader 18 and prescription label printer 20, and further includes conventional monitor 22 and keyboard 24. Computer 16 is preferably a conventional personal computer operated as a special purpose computer in accordance with the present invention but could also include a mainframe computer, minicomputer, or a computer network operable to run a wide variety of applications for a pharmacy. Computer 16 is also operable to access a plurality of databases represented by databases 26 in FIG. 1. These databases include a prescription database, an attribute database, a medicament database and a language translation database. As will be appreciated, databases 26 may be stored locally such as on the hard drive of computer 16 or may be stored remotely such as on a server computer or central pharmacy computer.

Supply container 12 is a large bottle such as that used for storing large quantities of medicaments in bulk but could also be some other unit of use package such as a box containing a bottle of insulin. Container 12 includes container indicia such as bar code 28 thereon identifying the medicament contained therein, such as a pill, capsule, tablet, caplet, liquid, cream, inhaler, patch, syringe or drug in reconstitutable form, including the type of medicine and the strength. It will be appreciated that the container indicia could include other markings such as alphanumeric printing, or could be in other forms such as a magnetic strip or magnetic ink. Printer 20 is preferably an industrial quality, thermal transfer printer but could also be the type of conventional printer commonly used in pharmacies for printing prescription labels and, in the present invention, is operable to print prescription label 30 for application to vial 14.

In use and operation of apparatus 10, a prescription is entered into computer 16 and stored as prescription data. Computer 16 then accesses the prescription database and retrieves prescription data corresponding to the prescription being filled. This prescription data includes medicament data identifying the prescription medicament. The prescription may be entered locally using keyboard 24 or may have been entered at a different location such as an incoming order station.

When a prescription is ready for filling, the pharmacist or pharmacy technician prompts computer 16 to retrieve the prescription data and display selected data on monitor 22. This includes the location of the medicament supply from the medicament database. Also, computer 16 accesses the attribute database and displays an image of the medicament and, optionally, a word description of the medicament as well. This serves as an aid to ensure that the correct medicament is retrieved from supply.

After retrieving container 12 from supply, the pharmacist or pharmacy technician uses bar code reader 18 to read bar code 28 which provides container data representative thereof to computer 16. In the preferred embodiment, bar code 28 is a UPC code corresponding to the national drug code (NDC) number or the drug identification number (DIN), for example. Specifically, computer 16 converts the UPC to the NDC number or DIN number using the medicament database. If the bar code is scratched or otherwise unreadable, or absent, the NDC number or DIN number printed on the container can be entered manually by way of keyboard 24.

Computer 16 then compares the container data (NDC number or DIN number) with the prescription data including the medicament data to determine a match therebetween. If there is no match, computer 16 displays an alert notation on monitor 22 as an indicator to the pharmacist or pharmacy technician that container 12 may be the wrong container for the prescribed medicament. Without a match, computer 16 also prevents the printing of prescription label 30. In this way, a source of error is eliminated. That is, the present invention eliminates that type of error in which the incorrect supply container is retrieved from storage and used to fill a prescription. This includes that kind of error where the type of medicine is correct but is not the prescribed strength.

If there is a match, computer 16 activates printer 20 to print prescription label 30. The information on label 30 includes the standard information required for any prescription drug label but also includes word description 32, image 34 and auxiliary information 36.

Figure 2:
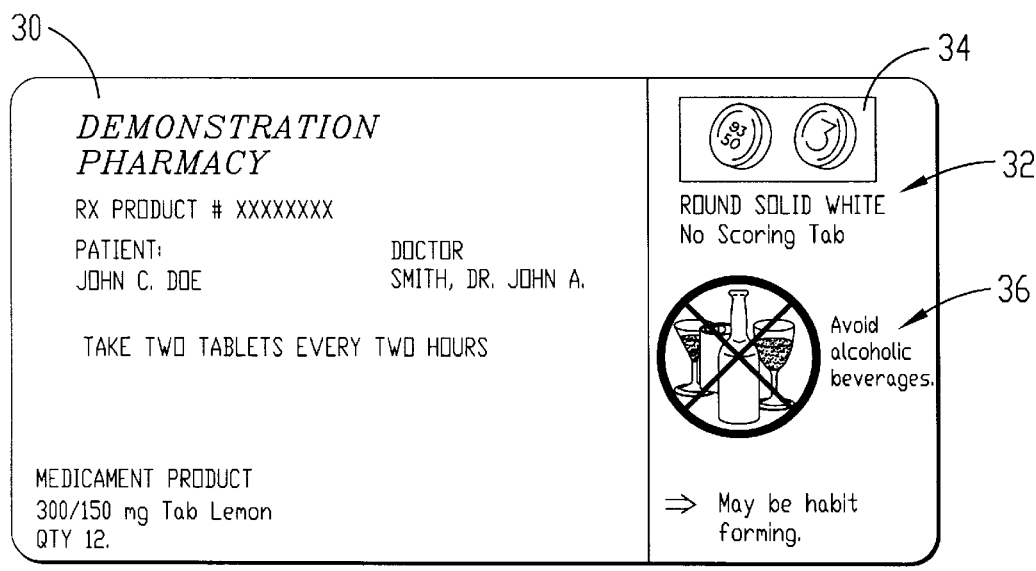
FIG. 2 is a representation of a prescription label printed by the apparatus of FIG. 1.

In the preferred embodiment, computer 16 activates printer 20 to print prescription label 30 with medicament indicia thereon representative of at least one physical attribute of the medicament. As illustrated in FIG. 2, the medicament indicia includes a word description 32 of the medicament. It is preferred that label 30 include both types of medicament indicia 32, 34, but some circumstances may indicate the printing of only one.

The preferred word description includes five fields: shape, color pattern, color, scoring and the form of the medicament. In the example of FIG. 2, these fields are round, solid (i.e., uniform color), white, no scoring and tab (tablet). If these words do not describe the medicament contained in the prescription package, the patient can identify this lack of a match. This may prevent the patient from taking the wrong medicament, or from not taking the correct medicament.

The preferred medicament indicia also includes an image 34 of the medicament. Some types of medicaments may require two images. For example, a tablet with opposed faces would be represented by two images, one for each face.

The attribute database includes data representative of the physical attributes described above (image 34 and word description 32) for a wide variety of medicaments. Preferably, the attribute database stores attribute data for all the medicaments that may be dispensed by the pharmacy.

As will be appreciated, the printing of medicament indicia on prescription label 30 may prevent the adverse consequences that occur when the prescription package contains a medicament other than one set forth in the prescription. That is, the word description or image of the medicament on the label may alert the patient that an error has occurred and thereby prompt the patient to have the error corrected.

Label 30 also includes auxiliary information 36 such as a caution "avoid alcoholic beverages," a warning "may be habit forming," and a representative symbol. In some prior art systems, a pharmacist or pharmacy technician must take the special step of determining what auxiliary information should be placed on the prescription label and then retrieve and apply corresponding pressure sensitive stickers to the prescription package. This is another source of potential error. The present invention includes the appropriate auxiliary information in the medicament database. Computer 16 retrieves this information and prompts the printing thereof on label 30. This avoids a potential error in which the pharmacist or pharmacy technician forgets to apply the auxiliary information stickers or applies the wrong stickers.

Apparatus 10 also enables the prescription label 30 to be printed in a second language. In the preferred embodiment, the prescription data that is entered into computer 16 also includes a pointer or other indication as to whether the patient requests the printing of prescription data in a second language other than the default language, such as English. If such is the case, computer 16 accesses the language translation database for language data corresponding to the second language equivalent (translation) of the prescription data. Computer 16 then supplies this language data to printer 20 and activates printer 20 to print the prescription data in the second language on prescription label 30.

In the alternative, computer 16 could activate printer 20 to print an additional label in the second language instead of printing the prescription label in the second language. With the option available of printing a prescription label in a second language, or printing information in both languages on the label, another source of error is eliminated in which the patient does not follow the label instructions because the patient cannot read the language in which the label is printed.

The present invention is also useful with systems other than preferred apparatus 10. For example, the invention could be used with an automatic prescription dispensing machine such as the SP 200 available from ScriptPro of Mission, Kans.

Those skilled in the art will appreciate that the present invention encompasses many variations in the preferred embodiments described herein. For example, the various features provided by the present invention may be optionally selected or disabled depending upon the needs of the pharmacy.

Having thus described the preferred embodiments of the present invention, the following is claimed as new and desired to be secured by Letters Patent:

1. A method of filling a prescription for a medicament including a designated amount of the medicament, said method comprising:

(a) retrieving a supply container of medicament corresponding to the prescription, there being prescription data corresponding to the prescription including the medicament stored in a computer, the container having machine-readable container indicia thereon representative of the medicament therein;

(b) using an indicia-reading device coupled with said computer to read said container indicia, to produce container data representative thereof, and to provide said container data to said computer;

(c) in said computer, comparing said container data and said prescription data to determine a match therebetween;

(d) only if a match in step (c), prompting a printer to print a package label representative of said prescription, said package label including medicament indicia representative of at least one physical attribute of the prescription medicament;

(e) removing the designated amount of medicament from said container and placing said designated amount into a package; and (f) applying said package label to said package.

2. The method of claim 1, step (d) including step of printing a word description of the medicament as said medicament indicia on said package label.

3. The method of claim 2, step (d) including the step of printing at least one of the shape, color pattern, color, scoring and form of the medicament as said medicament indicia on said package label.

4. The method of claim 1, step (d) including the step of printing an image of the medicament as said medicament indicia on said package label.

5. The method of claim 4, the medicament having opposed faces, step (d) including the step of printing an image of both of said opposed faces as said medicament indicia on said package label.

6. The method of claim 1, the computer including a database of medicament data representative of selected physical attributes of selected medicaments including the prescription medicaments, step (c) including the step of retrieving medicament data corresponding to said prescription medicament from said database, step (d) including the step of printing medicament indicia corresponding to retrieved medicament data on said package label.

7. The method of claim 1, step (d) including the step of printing said package label corresponding to said prescription in a selected language.

8. The method of claim 1, said prescription label being a first prescription label, step (d) including one of the steps of printing selected prescription data on said first prescription label in both a first and a second selected language, and printing a second prescription label corresponding to said prescription in a selected language different from the language of said first prescription label.

9. The method of claim 1, step (d) including the steps of printing the shape, color pattern, color, scoring and form of the medicament as said medicament indicia on said prescription label and printing an image of the medicament as said medicament indicia on said prescription label.

10. The method of claim 9, said container indicia including a bar code, said indicia reading device including a bar code reader, step (b) including the step of using said bar code reader to read said bar code.

11. The method of claim 1, said container indicia including a bar code, said indicia reading device including a bar code reader, step (b) including the step of using said bar code reader to read said bar code.

12. The method of claim 1, said bar code being a UPC code corresponding to one of the national drug code (NDC) number and the drug identification number (DIN), step (b) including the step of determining one of the national drug code (NDC) number and the drug identification number (DIN) corresponding to said medicament as said container indicia from said bar code.

13. The method of claim 1, step (d) including the step of prompting a printer to print said label with auxiliary information corresponding to said medicament.

14. The method of claim 1, step (b) including the step of manually entering said container data into said computer when said container indicia is unreadable by machine.

15. The method of claim 1, step (a) including at least one of the steps of displaying the location of said supply container, displaying a word description of the medicament, and displaying an image of the medicament on a monitor coupled with said computer.

16. A medicament-dispensing apparatus for filling a prescription for a medicament including a designated amount of the medicament, said apparatus comprising:

a prescription database including prescription data corresponding to a prescription to be filled including the medicament thereof;

a computer including means for accessing said prescription database for retrieving prescription data therefrom corresponding to the prescription to be filled;

a printer coupled with said computer and operable to print a prescription label representative of the prescription;

an indicia-reading device coupled with said computer and operable to read container indicia on a supply container of a medicament, said container data being representative of the medicament contained in the container, said device being operable to provide said container data to said computer, said computer including means for comparing said container data and said prescription data to determine a match therebetween and in response, prompting said printer to print the prescription label; and an attribute database including attribute data representative of at least one physical attribute of the medicament, said computer including means for accessing said attribute database and for retrieving attribute data therefrom corresponding to the prescription medicament and for activating said printer to print the prescription label with medicament indicia thereon representative of at least one physical attribute of the prescription medicament.

17. The apparatus of claim 16, said container indicia including a bar code, said indicia-reading device including a bar code reader.

18. The apparatus of claim 16, said medicament indicia including at least one of the shape, color pattern, color, scoring and form of the medicament.

19. The apparatus of claim 16, said medicament indicia including at least one image of the prescription medicament.

20. The apparatus of claim 19, the medicament indicia including a shape, color pattern, color, scoring and form of the prescription medicament.

21. The apparatus of claim 16, the prescription label being printed in a first language, said apparatus including a language database of language data representative of the prescription in a second language, said computer having means for accessing said language database and retrieving language data therefrom corresponding to a prescription, and for activating said printer to print a second prescription label in said second language.

22. The apparatus of claim 16, the prescription label being printed in a first language, said apparatus including a language database of language data representative of the prescription in a second language, said computer having means for accessing said language database and retrieving language data therefrom corresponding to a prescription, and for activating said printer to print additional prescription data thereon corresponding to said second language.

23. The apparatus of claim 16, said bar code being a UPC code corresponding to one of the national drug code (NDC) number and the drug identification number (DIN) corresponding to said medicament, said computer being operable to determine one of said NDC number and DIN number from said bar code.

24. The apparatus of claim 16, said prescription database including data representative of auxiliary information corresponding to said medicament, said computer including means for prompting said printer to print said label with said auxiliary information.

25. The apparatus of claim 16, further including means for manual entry of said container data.

26. The apparatus of claim 16, said computer including means for displaying at least one of the location of a supply container corresponding to the medicament of the prescription, a word description of said medicament, and an image of said medicament.

27. A method of filling a prescription for a medicament including a designated amount of the medicament, said method comprising:
   (a) receiving prescription data into a computer corresponding to a prescription to be filled, the prescription data including data representative of the prescription medicament;
   (b) in said computer, retrieving attribute data including a word description of the medicament from an attribute database, said attribute data being representative of at least one physical attribute of the prescription medicament;
   (c) printing a prescription label with prescription data thereon representative of the prescription and with medicament indicia corresponding to said attribute data.

28. The method of claim 27, step (b) including the step of retrieving at least one of the shape, color pattern, color, scoring and form of the medicament as said word description.

29. The method of claim 27, step (b) including the step of retrieving image data representative of at least one image of medicament as said attribute data, step (c) including the step of printing the prescription label with an image of the medicament as said medicament indicia.

30. The method of claim 27, the medicament having opposed faces, step (b) including the step of retrieving data representative of images of the opposed faces of the medicament.

31. A medicament-dispensing apparatus for filling a prescription for a medicament including a designated amount of the medicament, said apparatus comprising:
   a attribute database including attribute data corresponding to at least one physical attribute of the prescription medicament of a prescription to be filled, said attribute data including a word description of the medicament;
   a computer including means for accessing said attribute database for retrieving attribute data therefrom corresponding to the prescription to be filled; and
   a printer coupled with said computer and operable to print a prescription label representative of the prescription,
   said computer including means for activating said printer and print a prescription label with medicament indicia thereon corresponding to said attribute data.

32. The apparatus of claim 31, said attribute data including at least one of the shape, color pattern, color, scoring and form of the medicament.

33. The apparatus of claim 31, said attribute data including image data representative of an image of the medicament, said medicament indicia including an image of the medicament.

34. The apparatus of claim 33, the medicament having opposed faces, said medicament indicia including images of both said faces.

35. The apparatus of claim 33, said attribute data including at least one of the shape, color pattern, color, scoring and form of the medicament.

36. A prescription-filling apparatus for filling a prescription for a medicament including a designated amount of the medicament, said apparatus comprising:
   a language database including language data corresponding to the prescription in a second language;
   a computer including means for accessing said language database for retrieving language data therefrom corresponding to the prescription to be filled; and
   a printer coupled with said computer and operable to print a prescription label representative of the prescription,
   said computer including means for activating said printer to print a prescription label with prescription data thereon corresponding to said second language, said computer further includes means for activating said printer to print a first prescription label in a first language and a second prescription label in said second language.

37. The apparatus of claim 36, said computer including means for activating means for said printer to print a first prescription label in a first language and a second prescription label in said second language.

* * * * *

(12) EX PARTE REEXAMINATION CERTIFICATE (8791st)
United States Patent
Coughlin et al.

(10) Number: US 6,155,485 C1
(45) Certificate Issued: Jan. 10, 2012

(54) MEDICAMENT DISPENSING STATION

(75) Inventors: Michael E. Coughlin, Overland Park, KS (US); Christopher J. Thomsen, Kansas City, MO (US); Claire P. Coughlin, Overland Park, KS (US)

(73) Assignee: Scriptpro LLC, Mission, KS (US)

Reexamination Request:
No. 90/007,995, Jun. 16, 2006

Reexamination Certificate for:
Patent No.: 6,155,485
Issued: Dec. 5, 2000
Appl. No.: 09/188,734
Filed: Nov. 9, 1998

(51) Int. Cl.
*G06F 19/00* (2006.01)
*G06K 17/00* (2006.01)

(52) U.S. Cl. .......................... 235/383; 235/456
(58) Field of Classification Search .......... None
See application file for complete search history.

(56) References Cited

To view the complete listing of prior art documents cited during the proceeding for Reexamination Control Number 90/007,995, please refer to the USPTO's public Patent Application Information Retrieval (PAIR) system under the Display References tab.

*Primary Examiner*—Pia Tibbits

(57) ABSTRACT

A preferred medicament dispensing station (10) includes a computer (16) with a bar code reader (18) and a printer (20) coupled therewith. When filling a prescription from a supply container (12) of a medicament, the bar code reader (18) scans the bar code (28) on the container (12) and a computer (16) compares the bar code data with prescription data to determine a match before activating a printer (20) to print a prescription label (30) for the prescription. The preferred station (10) also includes databases (26) including an attribute database and a language database. The computer (16) activates the printer (20) to print medicament indicia on the prescription label (30) representative of physical attributes of the medicament including a word description (32) such as the shape, color pattern, color, scoring and form and an image (34). The computer (16) is operable also to prompt the printer (20) to print prescription data on the same label or on a second label in a second language.

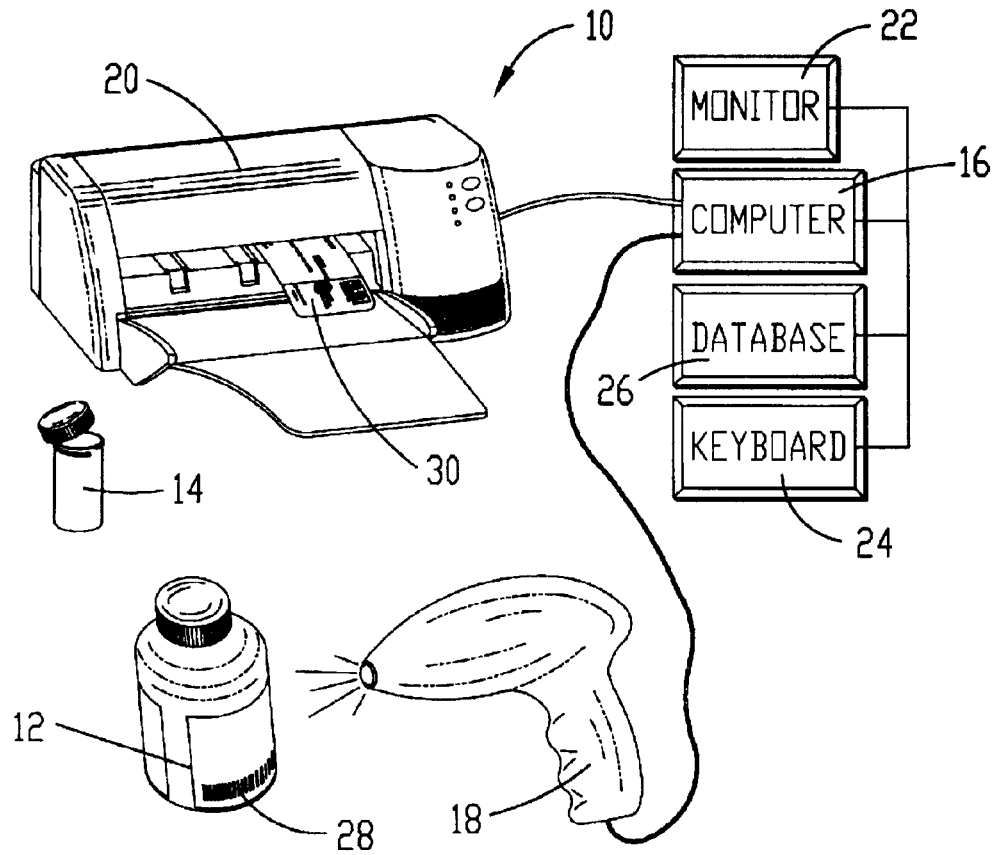

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-37 are cancelled.

* * * * *